(12) United States Patent
Schweiger (10) Patent No.: US 8,775,131 B2
(45) Date of Patent: Jul. 8, 2014

(54) METHOD, APPARATUS AND COMPUTER PROGRAM FOR PRODUCING A DENTAL PROSTHESIS

(75) Inventor: Josef Schweiger, Bergen (DE)

(73) Assignee: Josef Schweiger, Bergen (DE)

( * ) Notice: Subject to any disclaimer, the term of this patent is extended or adjusted under 35 U.S.C. 154(b) by 535 days.

(21) Appl. No.: 13/037,629

(22) Filed: Mar. 1, 2011

(65) Prior Publication Data

US 2011/0212419 A1      Sep. 1, 2011

(30) Foreign Application Priority Data

Mar. 1, 2010   (DE) .......................... 10 2010 002 484

(51) Int. Cl.
  *G06F 17/50*      (2006.01)
  *A61C 13/08*      (2006.01)

(52) U.S. Cl.
  USPC .......................................... 703/1; 433/202.1

(58) Field of Classification Search
  USPC .......................................... 703/1; 433/202.1
  See application file for complete search history.

(56) References Cited

U.S. PATENT DOCUMENTS

| 2004/0185422 | A1 | 9/2004 | Orth et al. | |
| 2005/0283058 | A1* | 12/2005 | Choo-Smith et al. | 600/315 |
| 2006/0063135 | A1 | 3/2006 | Mehl | |
| 2009/0246726 | A1* | 10/2009 | Chelnokov et al. | 433/24 |

FOREIGN PATENT DOCUMENTS

| DE | 19923978 | 10/2000 |
| DE | 102005042091 | 3/2007 |
| DE | 102005052838 | 5/2007 |
| DE | 102006033794 | 3/2008 |
| DE | 102007034005 | 1/2009 |
| EP | 1252867 | 10/2002 |

* cited by examiner

*Primary Examiner* — Dwin M Craig
(74) *Attorney, Agent, or Firm* — Duane Morris LLP; J. Rodman Steele, Jr.; Gregory M. Lefkowitz (57) ABSTRACT

A method for producing a tooth replacement and corresponding computer programs and devices are described. The method can comprise generating a tooth replacement having a core and an outer layer which define a boundary surface between each other. To ensure that the prepared tooth replacement is technically acceptable independent of skills and experience of the user and approximate the appearance of a natural tooth, the extension of the boundary surface represents a natural extension of the dentino-enamel junction of a tooth for which the tooth replacement is provided, wherein the extension of the boundary surface (i) is determined based on a recording of the dentino-enamel junction of the tooth for which the tooth replacement is provided, and/or (ii) is determined based on directly or indirectly recorded geometry data of at least a portion of the outer geometry of the tooth for which the tooth replacement is provided.

14 Claims, 4 Drawing Sheets

METHOD, APPARATUS AND COMPUTER PROGRAM FOR PRODUCING A DENTAL PROSTHESIS

CROSS-REFERENCE TO RELATED APPLICATIONS

This application claims priority to German Patent Application No. 10 2010 002 484.8, filed Mar. 1, 2010, which is hereby incorporated by reference.

FIELD OF THE INVENTION

The present invention relates to a method for producing a tooth replacement comprising the generation of the tooth replacement in particular with a one-piece core and an outer layer, in particular a one-piece outer layer, wherein the core and the outer layer define a boundary surface between each other. Furthermore, the present invention relates to a device for carrying out such a method and a computer program having program means which cause such a device to carry out such a method when the computer program is carried out on the device.

BACKGROUND

A two-piece tooth replacement having a scaffold made of, for example, zirconium oxide and a veneer made of, for example, siliceous ceramics is described in DE 10 2005 042 091 A1, wherein the tooth replacement is produced with the CAD/Cam method from two individual components which are connected to each other in a joining step. In DE 10 2005 042 091 A1, no indication can be found how the resulting boundary surface is geometrically predetermined.

DE 103 12 848 A1 discloses to form a tooth replacement part by using a tooth model and/or a tooth database, wherein the internal structure of the tooth model corresponds to the internal structure of an ideal tooth or is determined by means of an image prepared in advance of the individual tooth to be replaced/added, or, respectively, the tooth database reproduces tooth data of real existing teeth in digitalized form. In DE 103 12 848 remains unclear which aspects of the internal structure of a tooth are addressed, in particular, the dentino-enamel junction of a tooth is not addressed in DE 103 12 848 A1.

DE 199 23 978 A1 discloses a method for computer-assisted, patient-specific illustration and planning of dental and/or dental prosthetic work, wherein a digitalized database comprising a plurality of views of tooth models is used. The inner structure of a tooth or a tooth replacement is not addressed here.

In DE 102 52 298 B3, a method for producing tooth replacement parts or tooth restorations using electronic tooth representations is described. DE 102 52 298 B3 proposes a generic tooth model for modeling the outer geometry of a tooth or tooth replacement, wherein known data of the (remaining) tooth situation are used for adapting the generic tooth model to the individual case.

In the known prior art, the inner structure of a natural tooth, in particular the inner structure of that tooth for which a tooth replacement to be prepared is provided, is virtually disregarded. The inner structure of the tooth replacement to be prepared, in particular the extension of a boundary surface between a core and an outer layer of the tooth replacement, without consideration of the natural tooth structure and without defined rules, depends on the skills and the experience, for example, of the dental technician who monitors or performs the preparation of the tooth replacement.

SUMMARY OF THE INVENTION

One of the objects on which the present invention is based on is now to provide an aforementioned method, a corresponding device and a corresponding computer program by means of which the tooth replacement prepared therewith can fulfill the technical, in particular mechanical requirements for the tooth replacement largely independently of skills and experience of the user and, in terms of aesthetics, comes as close as possible to the desired appearance of a natural tooth.

According to the invention, one aspect of the aforementioned object is approached with the proposal of a method for producing a tooth replacement comprising the generation of the tooth replacement with, in particular, a one-piece and with, in particular, a one-piece outer layer, wherein the core and the outer layer define a boundary surface between each other, wherein the extension of the boundary surface represents a natural extension of the dentino-enamel junction of a tooth for which the tooth replacement is provided, wherein the extension of the boundary surface (i) is determined based on a recording of the dentino-enamel junction of the tooth for which the tooth replacement is provided, and/or (ii) is determined based on directly or indirectly recorded geometry data of at least a portion of the outer geometry of the tooth for which the tooth replacement is provided.

According to the invention, a further aspect of the aforementioned object is approached with the proposal of a device for carrying out such a method or a method according to any one of the dependent claims.

Furthermore, a further aspect of the aforementioned object is approached with the proposal of a computer program having program means which cause a device according to the invention to carry out a method according to the invention when the computer program is carried out on the device.

One of the findings on which the present invention is based on is that when reproducing the natural extension of the boundary surface between dentin material and enamel material in the natural tooth as comprehensive as possible, the material of the core of the tooth replacement quasi replaces the dentin of the tooth and the material of the outer layer of the tooth replacement replaces the enamel of the tooth in the region of the tooth replacement, whereby an appearance corresponding to the natural tooth can be reproduced in a simple manner without having to compromise features such as strength, elasticity or hardness of the restored tooth.

Furthermore, it was found that the determination of the dentino-enamel junction or the extension of the same can take place in a suitable manner, thus without completely destroying the tooth or the remainder of the tooth, directly on the tooth for which the tooth replacement is provided so as to allow a restoration as natural as possible. Such a determination of the extension of the boundary surface between natural dentin and natural enamel can be carried out, on the one hand, at a sufficiently early time and on the tooth, thus (long) before a damage or, on the other, after the damage and on the remainder of the tooth which is still available.

However, it was also identified that the present invention is not limited to the case in which the dentino-enamel junction itself can be recorded. It was found that for determining the extension of the boundary surface to be prepared it is also possible, i.e. additionally or alternatively, that the outer geometry or at least a portion of the still available outer geometry of the tooth can be used. Through the knowledge and in consideration of the processes by means of which a natural tooth is formed it was found that from the outer geometry of a tooth, the geometry of the boundary between enamel and dentin can be concluded.

It should be noted that with the invention, no reproduction of the boundary surface between natural dentin and natural enamel of the tooth to be replaced is intended which lies for example in the order of magnitude of individual cells or even finer, although this seems to be possible with appropriate effort. In a practical implementation it was found that the accuracy in the range from 20 µm to 100 µm, which can be achieved with the present technologies for preparing, for example, ceramic or plastic bodies, provides already very satisfying results, wherein a lower resolution or contour accuracy, for example in the range of 100 µm or even 200 µm, was also found to be sufficient.

It is known to use databases comprising tooth data sets in the field of dental restorations. However, the previously known databases relate only to a partial or also complete outer geometry of the teeth or tooth models. One aspect of the present invention considers using a database which is suitable for producing an inner tooth structure and was created, among other things, on the basis of an examination or measurement of natural teeth. The access to inner tooth structures is in particular of great advantage for a realistic reproduction of anterior teeth but also posterior teeth, as has been found by the inventors. The reason for this particular advantage is that by a multipart layer structure of the tooth replacement which is based on the structure of a natural tooth, an aesthetically appealing tooth replacement crown or dental bridge can be achieved particularly well.

Up to now, if layering in a conventional manner was provided for the structure of a replacement tooth, such layers were carried out manually by the dental technician. Thereby, the dental technician forms an inner structure as core onto which then an outer layer with transparent incisal compounds is applied. However, the resulting structure of the replacement tooth is exclusively based on the dental technician's skills and feeling gained through experience and is in no way associated with the natural inner structure of a tooth or even the tooth for which the tooth replacement is provided. The dental technician is focused on preparing a finished tooth replacement with the appearance of a natural tooth without having the will or the necessary information to reproduce the inner structure of the tooth.

Through an extensive use of computer-assisted manufacturing systems, the present invention allows to produce dental crowns from glass ceramics or lithium silicate ceramics using the CAD/CAM method without being limited here to the reproduction of only the desired outer shape. A desired aesthetic for the anterior tooth region can be achieved because a tooth provided with the tooth replacement produced according to the invention comes close to the natural tooth not only with respect to the outer geometry but also in terms of its inner structure.

While in conventional methods which provide a tooth replacement structure with core and outer layer, the inner tooth structures (which in the dental technician's jargon were sometimes called "dentin cores" without actually reproducing or representing natural dentin structures) were prepared in manual production by the dental technician, for example by growing and digitally copying or by reducing the anatomical outer shape by means of abrasive bodies and thus were based substantially on the experience of the dental technician, the present invention allows a completely computer-assisted production of a tooth replacement including the inner tooth structure, for example based on data from a database comprising information on natural teeth.

In one configuration of the method according to the invention, recording the dentino-enamel junction of the tooth takes place by means of computer tomography, in particular microcomputer tomography, sonography, radiography, close-range photogrammetry and/or photography.

The mentioned methods allow advantageously a non-invasive and non-destructive determination of the boundary surface between dentin and enamel, which boundary surface is located inside the tooth and thus is not directly accessible so that such a determination can take place independently of the necessity for a tooth replacement thus, while the tooth is not damaged yet. For example, the image of the dentino-enamel junction can be taken as soon as the tooth is fully developed.

In a further configuration of the method according to the invention, the indirectly recorded geometry data are determined from geometry data of the situation of the remainder of the teeth.

In particular, if in the case of an affected, damaged or even missing tooth, no complete or sufficient determination of the original geometry data of the original tooth can take place, it is advantageously still possible to use the geometry of the remainder of the teeth, thus, in particular adjacent and/or corresponding teeth, to draw conclusions on the geometry of the tooth to replaced.

In a further configuration of the method according to the invention, determining the extension of the boundary surface comprises virtually deforming the outer model geometry of a predetermined tooth data set for adapting to the outer geometry of the tooth for which the tooth replacement is provided, and virtually deforming a model boundary surface of the predetermined tooth data set corresponding to the deformation of the outer geometry for determining the boundary surface.

It was found that the geometry of the boundary surface between dentin and enamel of a natural tooth and the outer geometry of the natural tooth correlate in a sufficient manner so as to be able, based on the outer geometry of the tooth to be replaced and via an adaptation of the tooth model with data on geometry to the detected outer geometry, to determine the geometry of the boundary surface to be generated by adequate adaptation of the tooth model data on the dentino-enamel junction.

In a further configuration of the method according to invention, determining the extension of the boundary surface comprises determining a group of tooth data sets, wherein a predetermined average value of the outer model geometry of the group of tooth data sets corresponds to the outer geometry of the tooth for which the tooth replacement is provided, and determining the extension of the boundary surface by means of the predetermined average value of model boundary surfaces of the group of tooth data sets.

Alternatively or additionally to the aforementioned determination of the boundary surface geometry of the tooth data set to be prepared by an adapting "deformation" of model data, a combination of a plurality of tooth data sets can also be used. Said combination of a plurality of tooth data sets is determined in such a manner that the result of the application of an averaging algorithm for the data of the outer geometry of the tooth data sets corresponds to the indirectly or directly determined outer geometry of the tooth to be replaced (i.e. the outer geometry of the tooth to be replaced in the healthy, original state or the outer geometry of the combination of remaining tooth with prepared tooth replacement in the ideal case). If said averaging algorithm is applied accordingly also to the information provided via the tooth data sets on the boundary surface between enamel and dentin, this results in the desired extension of the boundary surface for the tooth replacement to be prepared.

In one embodiment of this configuration of the method according to the invention, the average value is determined by averaging the absolute and/or relative positions of predetermined reference points.

By selecting suitable reference points, for example in the form of characteristic points of the surfaces, the determination of the average value for a plurality of three-dimensional surfaces can be transferred into a determination of a plurality of position values, wherein characteristic properties of the respective tooth type are maintained.

In a further configuration of the method according to the invention, determining the extension of the boundary surface comprises determining a tooth data set, the outer model geometry of which meets a predetermined similarity criterion with respect to the outer geometry of the tooth for which the tooth replacement is provided, and determining the extension of the boundary surface based on the model boundary surface of the tooth data set.

In particular if the pool of available tooth data sets is large, it can be expected that within the plurality of these tooth data sets at least one data set exists which describes a tooth or a tooth model which, on the outside, corresponds to the tooth to be replaced so that the inner geometry of the same, thus the boundary surface between dentin and enamel stored in this data set, defines the boundary surface between core and outer layer for the tooth to be prepared. The higher the number of available tooth data sets, accordingly, the higher is the probability of a suitable tooth data set or the number of suitable tooth data sets, wherein the term "suitable" describes a similarity between the natural tooth to be replaced (in its original shape) and the geometry of the tooth data set, which similarity exceeds a predetermined degree. Different similarity degrees are known to the person skilled in the art which can be selected and/or combined according to the respective requirements of implementing the present invention.

In a further configuration of the method according to the invention, the model boundary surface of at least one tooth data set is determined based on a recording of the dentino-enamel junction of a natural tooth by means of computer tomography, in particular microcomputer tomography, sonography, radiography, close-range photogrammetry and/or photography and/or a recording of the outer geometry of the dentin of a natural tooth after removing the enamel.

Even if the data collection of tooth geometry data in the database of tooth data sets can be based entirely on a theoretical determination based on suitable models, the data collection on the basis of actual teeth including a data collection which is not entirely non-destructive is associated with the advantage that independent of potential deficits of a theoretical modeling, the preparation of tooth replacements according to the present invention is based on geometries of actual teeth.

In a more specific configuration of the method according to the invention, recording the dentino-enamel junction takes place by means of close-range photogrammetry and/or photography using light for which the enamel of the tooth is translucent, in particular using red light or light having a longer wavelength.

In connection with the present invention it was found that—although a natural tooth is usually opaque for the human eye in such a manner that inner structures are not visible—by selecting light which is able to pass sufficiently unhindered through the outer layer, thus the enamel of the tooth, recording inner structures in the form of the boundary surface between dentin and enamel is possible.

In a further configuration of the method according to the invention, the material or the materials for core and outer layer are selected such and/or generating core and outer layer is carried out such that the translucence of the outer layer is higher than the one of the core. Preferably, with respect to their translucence, the materials correspond to the natural materials dentin and enamel in terms of absolute values or in their relative ratio. The average light transmittance (direct transmission coefficient (tc) [%]) in the wavelength range from 400 to 700 nm for a sample with a thickness of 1 mm (measured with a spectral photometer DU-7 (Beckmann) after polishing with a 3 µm diamond for removing scratches) for the core lies preferably in the range from 20 to 65%, particularly preferred in the range from 40 to 60%. In contrast, for the outer layer as veneer layer, a translucence in the range of 65 to 95% is preferred, in particular in the range of 76.5 to 85%. In "Composite Resin Restorations-Natural Asthetics and Dynamics of Light" by S. Duarte et al. (Pract. Proced. Aesthet. Dent. 2003, 15(9); A-H) is specified that enamel (as material of the natural enamel layer) has a light transmittance/translucence of 70.1%, and dentin of 52.6%.

When setting the translucence of the outer layer in such a manner that it exceeds the translucence of the core, the aesthetic appearance of the tooth replacement can be adapted in a simple manner to the one of a natural tooth (in particular the one of the adjacent teeth).

In a further configuration of the method according to the invention, the core comprises or consists of an oxide-ceramic material, a silicate-ceramic material and/or a plastic material and/or the outer layer comprises an oxide-ceramic material, a silicate-ceramic material and/or a plastic material or consists thereof. Here, according to the above, a translucent, silicate-ceramic, in particular translucent glass-ceramic material is particularly preferred for the outer layer.

In the present context, silicate ceramics include in particular the following: Glass ceramics, leucite-reinforced glass ceramics, feldspar ceramics, leucite-reinforced feldspar ceramics, lithium silicate ceramics and fluoroapatite ceramics.

The aforementioned materials have already been used in practice so that adequate experience in terms of handling and use is available for the person having relevant skills, which experience can advantageously be used during the implementation of the present invention.

It should be noted that the hardness of the outer layer is of importance for the functionality of the restoration. It should not be too high because otherwise the opposing tooth would be excessively abraded. It should not be tool low either because otherwise the veneer would be ground off.

In a conventional restoration, the core of the present invention finds its equivalent in the combination of scaffold and the so-called "dentin layer". It is preferred that the core of the present invention has a strength which corresponds to the strength of the conventional scaffold or is higher. Preferred in the present case is a minimum strength of 100 MPa for individual treatments, 300 MPa for three-unit bridges in the anterior teeth region and 500 MPa in the posterior teeth region (values according to standard).

When selecting the materials and properties for the core and the outer layer and in case that ceramic materials are used which are bonded by firing in the furnace, preferably, the coefficient of thermal expansion (CTE) should be considered which can play an important role for the function of the treatment (i.e. the tooth replacement). If, during the cooling phase, the veneer ceramic (i.e. the outer layer) is subjected to compressive stress, this increases the stability of the veneer. Tensile stress in the veneer ceramic can result in cracks and spalling, thus in a failure. Therefore, the CTE of the veneer is preferably lower than the one of the inner core.

When selecting the material and the corresponding production, the abrasion resistance of the outer layer or, respectively, the abrasiveness of the material can also be considered and, preferably, should be considered. The selection of the material for the outer layer is preferably made in such a way that the material's abrasion values are largely approximated to the abrasion values of the natural tooth enamel so that the teeth in the opposite jaw are not excessively abraded during mastication.

BRIEF DESCRIPTION OF THE DRAWINGS

The invention is explained in more detail hereinafter with reference to the enclosed drawings.

DETAILED DESCRIPTION

Figure 1:
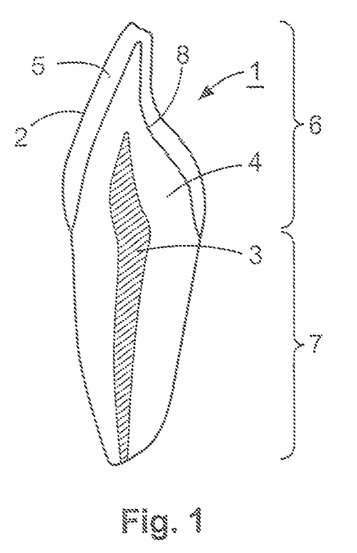
FIG. 1 shows a vertical sectional view of a natural, upper middle incisor.

FIG. 1 shows a vertical sectional view of a natural, upper middle incisor 1 having the outer surface 2 and the layered inner structure. The illustration of the tooth 1 schematically comprises dental pulp 3, dentin 4 and enamel region 5 (also called incisal shell). Principally, the whole tooth 1 can also be divided into a region of the natural tooth crown 6 and a region of the natural tooth root 7. In FIG. 1, among other things, the natural extension of the boundary surface 8 between dentin 4 and enamel 5 is shown.

Figure 2:
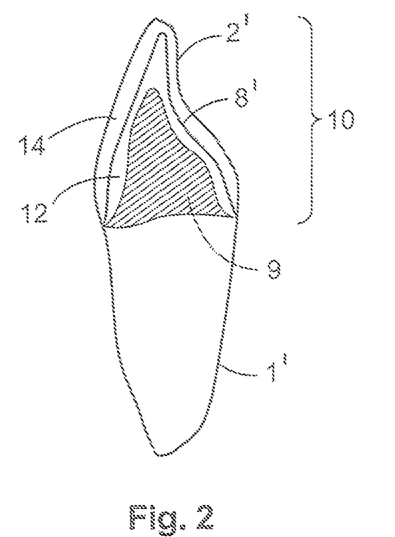
FIG. 2 shows a vertical sectional view of a tooth replacement part (crown) on an upper middle incisor, which replacement part was produced according to an embodiment of the invention.

FIG. 2 shows a vertical sectional view of a tooth replacement part (crown) on an upper middle incisor, which replacement part was produced according to an embodiment of the invention. The tooth replacement part 10, here an artificial crown, is arranged on a ground tooth stump 9 of an upper middle incisor 1' as remaining tooth, wherein the tooth replacement part 10 comprises a ceramic core 12 and a ceramic outer layer 14. With respect to its extension, the boundary surface 8' between core 12 and outer layer 14 corresponds to the boundary surface 8 of FIG. 1. Likewise, with respect to its extension, the outer surface 2' of the outer layer 14 corresponds to the outer surface 2 of FIG. 1. In case of the tooth replacement illustrated in FIG. 2, no additional reinforcement of the core 14 in the form of a high-strength scaffold is provided. With a sufficient strength of core 14 and/or outer layer 12, such a scaffold is not required. Producing the core 12, the outer shape 8' (thus the boundary surface between core 12 and outer layer 14) of which corresponds in the region of the tooth replacement 10 to the one of the dentin core 4 of FIG. 1, is carried out on the basis of a data set from a tooth structure database and by means of computer-assisted methods (in particular CAD/CAM and generative methods). Producing the outer layer 14 is carried out either manually by coating or by overpressing. Producing the incisal shell 14 can also be carried out on the basis of a data set of the tooth structure database and by means of computer-assisted methods (in particular CAD/CAM and generative methods). Artificial tooth crown 10 and natural tooth root 9 form an overall structure.

Although FIG. 2 shows a case in which the crown is placed onto a remainder of a tooth, the present invention is not limited to such a configuration. In particular, the invention can also be implemented in case of a crown on an implant, wherein then, preferably, the conventional components abutment and scaffold are preferably represented in the form of the core according to the invention. Furthermore, the invention is also not limited to the fact that the core is (fully) enclosed by the outer layer. In this respect, the present invention relates also to other possibilities such as, for example, preparing a tooth replacement on which only the front part of the tooth is replaced.

Figure 3:
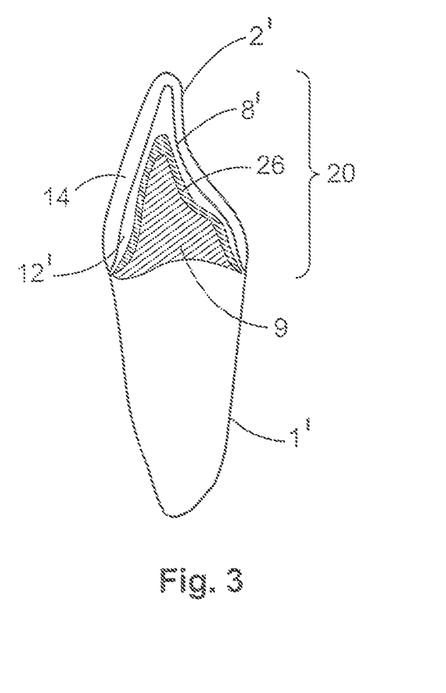
FIG. 3 shows a vertical sectional view of a tooth replacement part (crown) on an upper middle incisor, which replacement part was produced according to another embodiment of the invention.

FIG. 3 shows a vertical sectional view of a tooth replacement part (crown) on an upper middle incisor, which replacement part was produced according to another embodiment of the invention. Here, as in FIG. 2, the tooth replacement part 20 is an artificial crown and is arranged on a ground tooth stump 9 of an upper middle incisor 1'. The tooth replacement part 20 comprises a core having a high-strength scaffold structure 26 and a ceramic layer 12' applied thereon as well as an outer layer 14 which, in turn, is arranged on the ceramic layer 12' so that the outer layer 14 and the ceramic layer 12' form a boundary surface 8'. The outer layer 14 is made of an incisal compound or transparent compound and formed as incisal shell. Similar to the production of the tooth replacement shown in FIG. 2, the production of the ceramic layer 12' of the core is carried out on the basis of a data set from a tooth structure and by means of computer-assisted methods (in particular CAD/CAM and generative methods), wherein likewise for the production of the outer layer 14, for example, a manual production by coating or overpressing is provided. Moreover, producing the outer layer 14 can be carried out on the basis of a data set of the tooth structure database and by means of computer-assisted methods (in particular CAD/CAM and generative methods). Here too, the artificial tooth crown 20 and the natural tooth root 9 form an overall structure.

Figure 4:
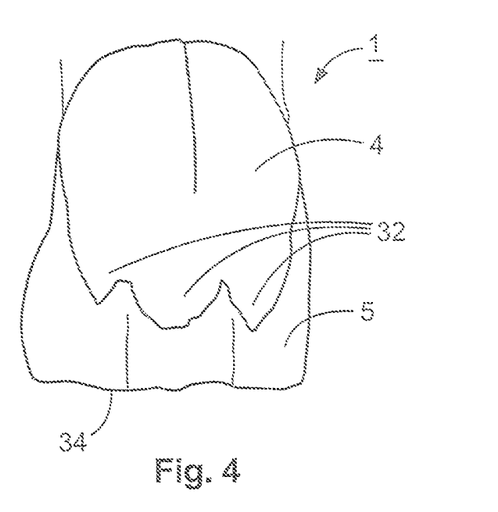
FIG. 4 schematically shows a front view of a natural, upper middle incisor with illustrated inner dentin core.

FIG. 4 schematically shows a front view of a natural, upper middle incisor 1 with illustrated inner dentin core 4 and illustrates its structured inner layered composition, wherein the formation of irregular structures of the dentin core towards the incisal edge 34 is clearly visible (so-called mamelons 32), as well as the irregular formation of the incisal edge 34 itself.

Figure 5:
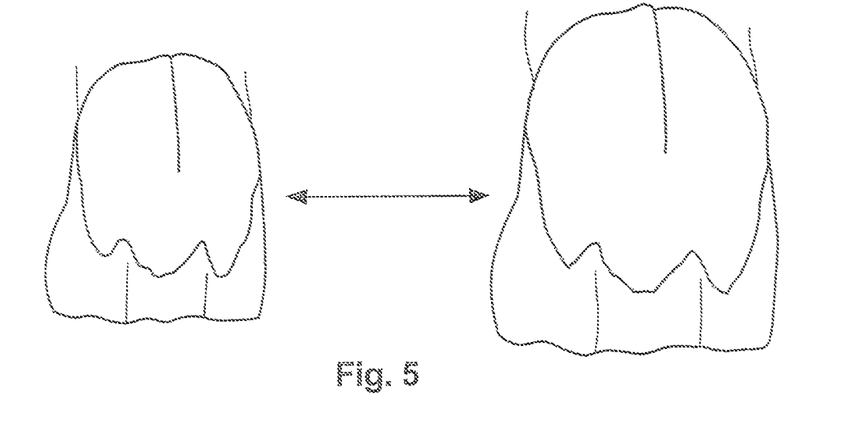
FIG. 5 illustrates a dynamically proportional change of an inner layered tooth structure (dentin core) corresponding to a change of the outer geometry.

FIG. 5 illustrates a dynamic proportional change of an inner layered tooth structure (dentin core) corresponding to a change of the outer geometry. The illustration in FIG. 5 (as well as in the following FIGS. 6 to 8) involves a visualization of geometrical data in a tooth data set and the manipulation or modification of the data. The individual elements illustrated in FIG. 5 correspond to the illustration of FIG. 4 so that a further explanation and repeating the reference numbers is not required. FIG. 5 shows how the data set visualized in the left region is transferred by proportional scaling into a data set which represents a larger tooth. However, the relative dimensional proportions of the individual tooth elements remain. Likewise, a data set can also be transferred into a data set which represents a smaller tooth.

Figure 6:
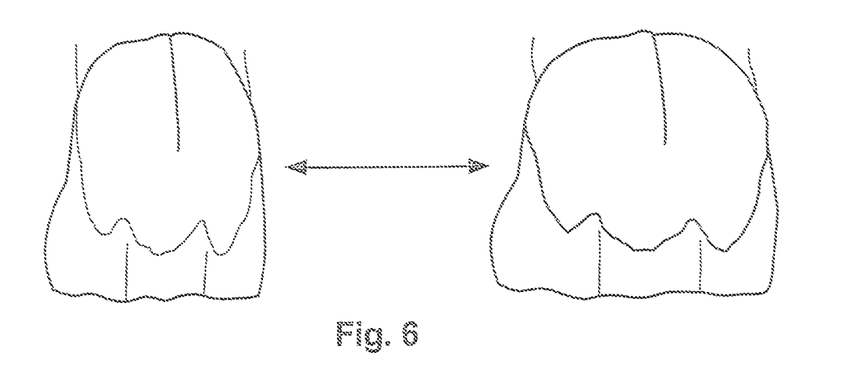
FIG. 6 illustrates a dynamically non-proportional change of an inner layered tooth structure (dentin core) corresponding to a change of the outer geometry.

FIG. 6 illustrates a dynamic, non-proportional change of an inner layered tooth structure (dentin core) corresponding to a change of the outer geometry. In case of the transfer illustrated in FIG. 6, no elongation or compression which is uniform in all dimensions takes place. Here, the scaling is not proportional so that in some cases, dimensional proportions (here height to width) are changed.

Figure 7:
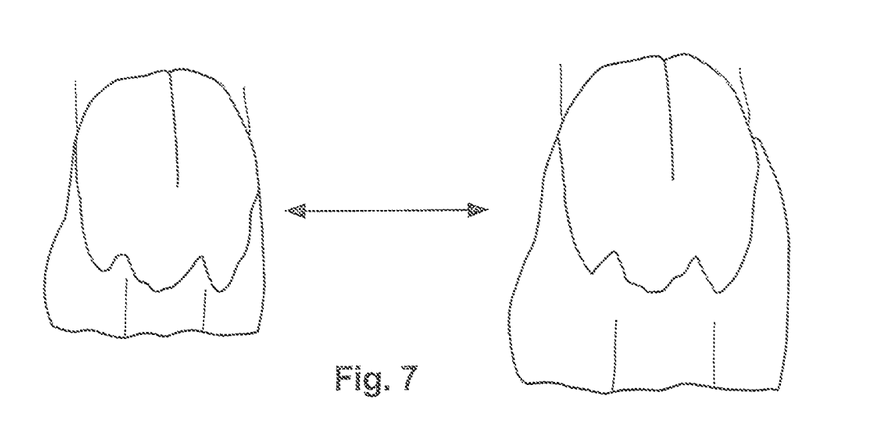
FIG. 7 illustrates a static non-change of an inner layered tooth structure (dentin core) with the outer geometry being changed.

FIG. 7 illustrates a static non-change of an inner layered tooth structure (dentin core) with the outer geometry being changed. In case of the transition shown in FIG. 7, the dentin structure remains unchanged with respect to size and shape, while the outer geometry as a whole changes its size.

The invention is not limited to the modifications shown in the FIGS. 5 to 7. In particular, other changes in the data sets are also possible which includes combining the scalings in FIGS. 5 to 7 with each other or with other changes in the data sets.

Figure 8:
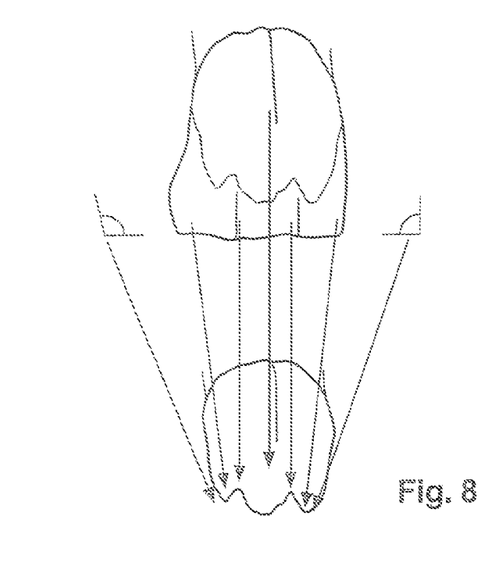
FIG. 8 illustrates the biogeneric correlation principle between outer tooth surface features and tooth shape features and the layered inner structure, in particular the dentin core.

FIG. 8 illustrates the biogeneric correlation principle between outer tooth surface and tooth shape features and the layered inner structure, in particular the dentin core. Here, a reduced number of specific points on the outer tooth surface and/or specific tooth shape and tooth surface features (e.g. mesial and distal angles of the corners of the incisal edge, curvature radii of the labial surface etc.) determine a defined geometry of the inner tooth structures, in particular of the dentin core. The angles indicated in FIG. 8 symbolize the shape of the rounding of mesial and distal edge of an anterior tooth. In many cases, the mesial edge of a incisor is less rounded than the distal edge. The angle formed in this manner then appears mesially with approximately 90° whereas the distal edge of an incisor has a larger rounding and thus, the angle is greater than 90°. In technical terminology, this feature is called "angle feature". The arrows illustrate the relationship and the dependency between the features of the outer surface and the features of the inner surface.

Figure 9:
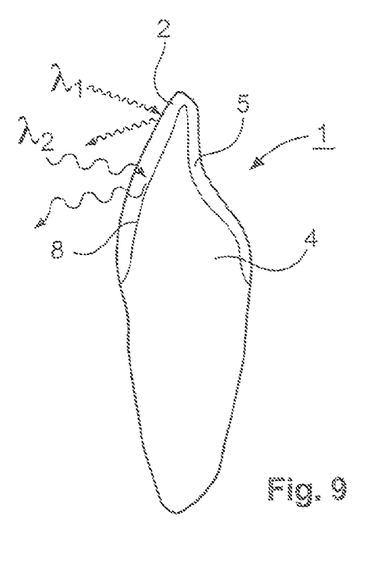
FIG. 9 illustrates light-optical behavior on layers of an upper middle incisor.

FIG. 9 illustrates light-optical behavior on layers of an upper middle incisor. FIG. 9 shows the different light-optical behavior of incisor 5 and dentin core 4 using the example of a sectional view through an upper middle incisor 1. The illustration of FIG. 9 corresponds to the one of FIG. 1 but with the pulp 3 being omitted. By using different wavelengths, besides the tooth surface 2, the lower inner layered tooth structures (in particular the boundary surface between dentin core 4 and enamel 5) can also be recorded digitally and three-dimensionally by 3D detecting units, in particular when using light having a long wavelength, e.g. infrared light or infrared laser light. The operating mode of 3D detecting units is principally known. Known devices operate, for example, on the basis of structured-light triangulation, laser light triangulation or video signal. The wavelength $\lambda_1$ is smaller than the wavelength $\lambda_2$. The wavelength $\lambda_1$ represents, for example, blue light with a short wavelength which is reflected on the outer surface 2 of the tooth 1, whereas $\lambda_2$ represents, for example, red light with a longer wavelength or infrared light which penetrates through the enamel region 5 and is reflected only on the boundary surface between dentin 4 and enamel 5. In this manner it is virtually possible to look into the tooth.

Figure 10:
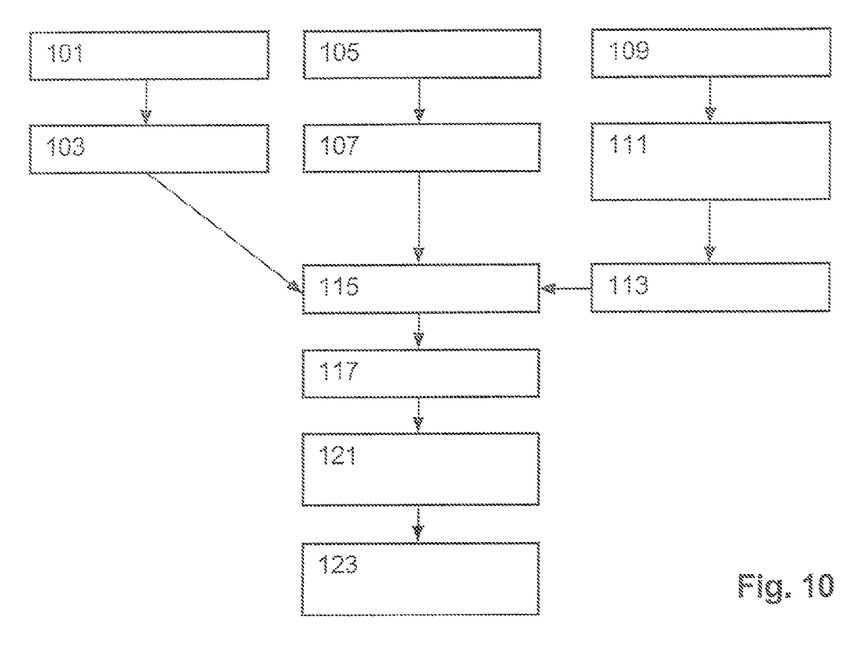
FIG. 10 schematically shows method steps of an embodiment of the method according to the invention.

FIG. 10 schematically shows method steps of an embodiment of the method according to the invention in three alternatives. Shown is a basic workflow for using a database having data sets of the outer tooth surface and data sets of the inner layered structure as well as the dynamic correlation. As an example, a distinction is made between three possibilities for the use of the database with dynamic or static correlation.

In a first case, a mirror image of the missing tooth is available and is recorded as data set (step 101). Said data set is axisymmetrically mirrored about the vertical tooth axis (step 103) and subsequently, the data set which is most similar with respect to its outer tooth surface is selected from the database (step 115), for example by means of the "best fit alignment" method. Since for each outer tooth surface recorded as data set, a correlation (dynamic and static) to data of the inner layered tooth structure exists in the tooth database, data of the inner layered tooth structures can be retrieved, in particular data on dentin core and incisal shell or on the boundary surface between dentin core and incisal shell (step 117). These data are then used via computer-assisted manufacturing devices (in particular CAD/CAM, generative methods) for producing the components of the tooth replacement to be prepared (step 121). The final completion of the tooth replacement part is subsequently carried out by manual coating (in particular ceramic and plastic), by pressing on and overpressing or by connecting the individual computer-fabricated layers by adhesive bonding or sintering (step 123).

In a second possibility it is identified that no mirror image of the missing tooth is available (step 105), wherein then, for example based on subjective criteria, the user selects the database's data set which is most suitable with respect to its outer tooth structure (step 107). This data set of the outer tooth structure is then used for the further manufacturing process as described above (steps 115, 117, 121, 123).

In a third possibility, again, no mirror image of the missing tooth is available (step 109). The data set of an adjacent tooth or a jaw section (e.g. upper anterior jaw) which is most similar with respect to its outer tooth surface is selected from the database (step 111), for example by means of the "best fit alignment" method. The data set of the jaw section consists of the individual data sets of the outer tooth structures of the tooth types contained in this jaw section (e.g. upper anterior jaw section 1 to 3, lower anterior jaw section 1 to 3, posterior tooth jaw section 4 to 8). Due to the correlation within the data set of the jaw section, the adjacent tooth which is most suitable with respect to its outer tooth surface can be associated with the most suitable data set of the outer tooth structure of the missing tooth (step 113). This data set is then used as described above for the further manufacturing process (steps 115, 117, 121, 123).

Figure 11:
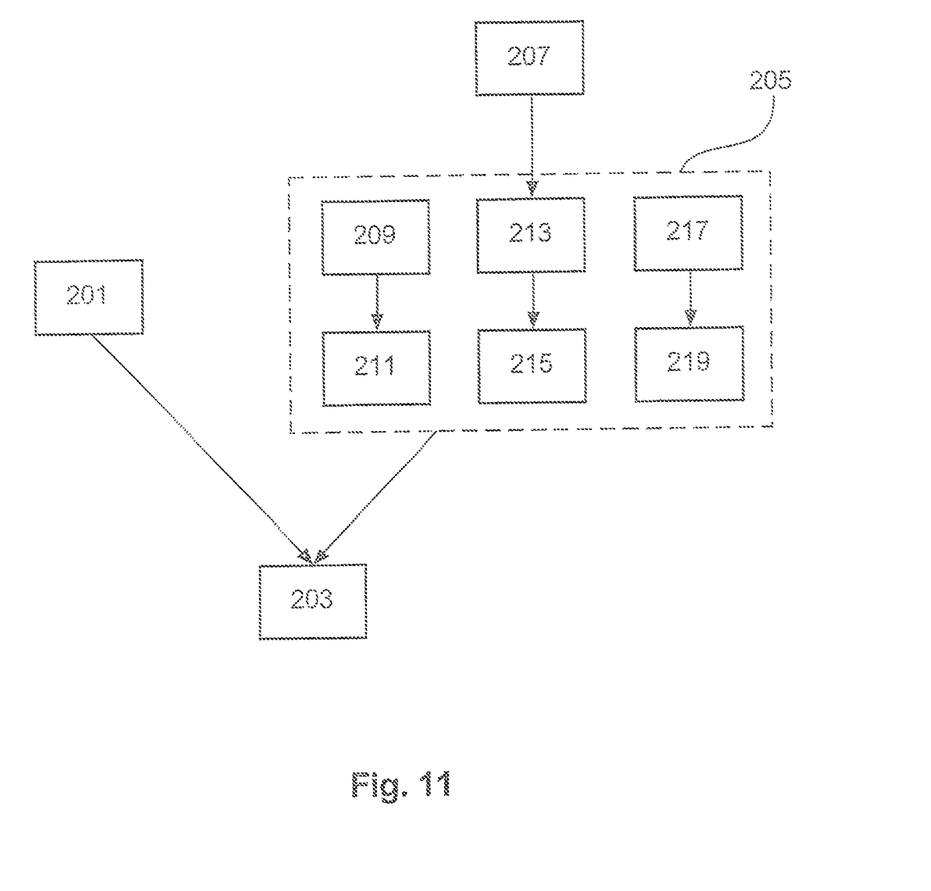
FIG. 11 schematically shows a process flow of an embodiment of the method according to the invention.

FIG. 11 schematically shows a process flow of an embodiment of the method according to the invention, wherein—same as in FIG. 10—it is not necessary according to the invention to run through all method steps if alternatives are available.

In step 201, the extension of the boundary surface between the core and the outer layer of the tooth replacement is defined based on a recording of the dentino-enamel junction of the tooth for which the tooth replacement is to be prepared, wherein the data of the boundary surface are then used in step 203 for generating, i.e. producing the tooth replacement.

As indicated with step 205, an alternative or addition to this is to use the outer geometry of the tooth to be replaced, wherein the geometry data are recorded directly (for example by direct measuring or scanning) or indirectly (for example by recording the geometry data of the remainder of the teeth, in particular the opposing tooth and/or adjacent teeth and/or mirror-imaged counterparts in the set of teeth). Here, the data are determined in step 207 from geometry data of the actual (or previously recorded) situation in the oral cavity of the patient if the data of the tooth to be replaced are not sufficient or are not available at all.

In the illustration of FIG. 11, step 205 comprises three alternatives which can also be linked to one another so as to achieve a further improvement of the determination of the extension of the boundary surface.

In one alternative, the outer geometry of a tooth model (tooth data set) is virtually deformed in step 209 in such a manner that said deformed outer geometry corresponds to the outer geometry of the tooth (in the healthy state) for which the tooth replacement is provided. The corresponding deformation (e.g. scaling, distortion, torsion) is then mathematically applied to the data of the model boundary surface so as to obtain data in step 211 on the extension of the boundary surface between core and outer layer of the tooth replacement for preparing the tooth replacement.

In another alternative, a group of tooth data sets is determined in step 213 which are selected such that a predefined averaging algorithm, when used for the outer geometry data of said data sets, approximates the outer geometry of the tooth to be replaced. This algorithm is then applied in step 215 to the data on the extension of the natural dentino-enamel junction in the data sets so as to once again obtain data for preparing the tooth replacement having the boundary surface according to the invention.

In a third alternative, a tooth data set is selected in step 217, the outer geometry data of which are sufficiently similar to the outer geometry data of the tooth replacement (or tooth in the healthy state) to be prepared, i.e. the mathematical determination of which achieves a sufficiently good value above or below a predetermined threshold. The data in said data set are then used for determining the extension of the boundary surface between core and outer layer for the preparation according to the invention of tooth replacements (step 219).

A particular advantage of the present invention is that the invention allows to generate not only fully anatomical teeth by means of computer-assisted manufacturing technologies, in particular CAD/CAM, but also a tooth replacement, the inner structure of which is based on a natural tooth. The core provided by the invention, the outer shape of which corresponds to the outer shape of a natural dentin core of a tooth offers the advantage, in particular in the anterior tooth region, that by applying coats of incisal compounds, highly aesthetic restorations can be achieved in a fast and effective manner which have a better aesthetic effect compared to fully anatomical, milled restorations which do not consider the inner structure of the tooth. Up to now, for preparing a multilayered tooth replacement, a so-called cut back technique" for manually removing the incisal region from a fully anatomical tooth crown was provided resulting in additional work for the dental technician. Moreover, the inner structure of the tooth replacement achieved in such a manner is purely based on the imagination of the dental technician and is independent of an actual natural structure of a tooth.

The inner core provided according to the invention is advantageously generated in particular based on data from a database on the basis of scanned natural teeth and allows a very natural reproduction of the natural tooth to be replaced.

In a first test of the present invention, the tooth replacement was produced from glass-ceramic blocks. However, other materials, for example oxide-ceramic materials, are principally also possible for the use in connection with the present invention. Thus, it is absolutely possible to use zirconium dioxide with adequately selected translucence (preferred 40% to 60%, see above) as material for the core of the tooth replacement according to the invention. One of the advantages is that it is possible, for example, to produce anatomically partially reduced (thus with inner core structure according to the invention), solid ceramic bridges by means of computer-assisted systems.

One aspect of the present invention relates to a tooth structure database which reproduces teeth in digitalized form, wherein the surface of the tooth has a correlation to the layered inner tooth structures. A further aspect relates to a method for detecting outer tooth surfaces, the associated layered inner tooth structures, and a method for determining the correlation between the outer tooth surfaces and the specifically associated layered inner tooth structures.

By far the largest portion of the human tooth consists of dentin which forms the first "protective casing" for the pulp located therein. The pulp is colloquially also called "dental nerve". The main component is loosely bonded connective tissue with numerous cells, intercellular basic substance, reticular as well as collagen fibers and not least nerves and vessels. The dentin in turn is covered in the crown region by dental enamel and in the root region by root cementum. Enamel, dentin and cementum together represent the hard tooth substance of the human tooth. Here, the dental enamel is the hardest substance of the human body with a Vickers hardness of 250-550 and a compression strength of 300-450 MPa. The enamel's Young's modulus is 50,000-85,000 MPa. In contrast, the dentin is significantly more elastic (Young's modulus 15,000-20,000 MPa) because it comprises a considerably higher proportion of organic substance. The Vickers hardness of the dentin is 60-70 and the compression strength is approximately 200-350 MPa. With respect to its structure and also hardness, the root cementum is similar to a human bone without being vascularized like the latter. The cementum belongs already to the periodontium because the periodontal fibers, which movably anchor the teeth in the alveole, are attached thereto. In contrast to the nature, restorations are not limited to individual teeth. Moreover, in the form of bridges, they can also cover tooth spaces. In such a case, the restoration has to withstand considerably higher bending loads than, for example, the natural dentin.

Currently, there are many computer-assisted manufacturing methods which offer no database for the production of teeth. However, some systems offer databases which are based on data of scanned prefabricated plastic teeth or have been created by manual coating by dental technicians.

With the so-called "biogeneric occlusal surface" of the Cerec-System of the company Sirona (Bensheim-Germany) which is described in DE 102 52 298 B3 and has been developed by Prof. Dr. Albert Mehl, the attempt is made, based on several thousand scanned teeth and by means of remaining tooth substance of the tooth to be replaced, to calculate a most suited tooth geometry from said database for the missing tooth portions. The goal is, to achieve a comparatively natural geometry of partial crowns (inlays, onlays). The use of the "biogeneric tooth model" exists only in the posterior tooth region. In case of the biogeneric tooth model, missing tooth substance of the outer tooth surface is supplemented by optimizing a generic tooth model data set of the desired tooth stump with respect to the still existing remaining tooth substance and/or opposite teeth and/or adjacent teeth and/or bite impression. The application of the biogeneric principle with respect to the layered inner tooth structure is not described in the aforementioned patent specification.

Furthermore, a tooth database is known from DE 103 12 848 A1. This document addresses in an unspecific and general manner the aspect of the inner structure of a tooth without discussing details or even the dentin-enamel junction of a natural tooth. An inner surface, for example in the posterior region, can be the tooth surface located inwardly on the occlusal surface and facing toward the tooth fissure (=groove-like depression in the occlusal surface) or, in the anterior tooth region and posterior tooth region, the tooth surface facing inwardly toward the palate or the tongue. An inner structure of the described tooth model can be the bead-like shape on the tooth surface facing inwardly toward the tooth fissure (=groove-like depression in the occlusal surface), thus the relief of the occlusal surface or, in case of the anterior tooth, the tooth's relief-like structure on the inner side of the tooth (facing toward the palate or tongue). The question of the inner structure of a tooth can also relate to the subdivision into pulp on the one hand and the combination of dentin and enamel on the other.

The company Sirona offers a database for the Cerec-System in which, in the anterior tooth region, the user is given a mamelon structure (finger-like warpages of the dentin toward the incisal region) generated according to static, geometrical design guidelines, which mamelon structure can then be reproduced in an output device.

In the dissertation of Mr. Florian Andreas Probst ("Dreidimensionale Untersuchungen zur Morphologie der oberen Frontzähne"—dissertation for the doctoral degree in dentistry at the Medical Faculty of the Ludwig-Maximilians-University in Munich, presented by Florian Andreas Probst, Dachau (2007), rapporteur Prof. Dr. Dr. Albert Mehl), the latter describes in detail the three-dimensional morphology of the upper anterior teeth. This paper, too, does not address the inner three-dimensional layered structure of these teeth.

It can be summarized that currently, no databases for the three-dimensional inner layered structure of teeth in the anterior and posterior region are available. Here, the term "tooth structure database" is to be understood as a database/library which comprises the three-dimensional layered inner structures and the associated surfaces of the respective specific teeth in digitalized and/or actually existing form.

Likewise, there is no method for automatic generation of the layered inner tooth structure, in particular the dentin core. However, this would be very important because therewith, the production cost for tooth replacements can be decreased and the cost efficiency of CAD/CAM systems can be increased.

In connection with the present invention, a tooth structure database is created which considers the outer morphology (surface) as well as the inner layered structure (dentin and enamel) of teeth and allows in particular a defined dynamic correlation and/or static correlation and/or biogeneric correlation between the outer morphology and the inner layered structure of teeth. Also to be mentioned here is a method which allows recording the inner layered structure of teeth. The recorded data can be based on natural teeth as well as artificially prepared teeth.

The term "correlation" is to be understood here as the allocation of a data set describing the inner layered structure to the data set describing the outer geometry of said tooth. Also, "correlation" is to be understood here as the allocation of a data set describing the outer tooth geometry of a tooth of a jaw section (e.g. $1^{st}$, $2^{nd}$, $3^{rd}$, $4^{th}$ quadrant) to a data set describing the outer surface of another tooth of the same or another jaw section. In both applications, the correlation is preferably empirically determined e.g. using natural teeth, determined through mathematical calculation or defined by dental models.

Recording data for the present invention can be carried out in different ways which are explained exemplary below.

A three-dimensional recording of tooth data can take place by scanning extracted teeth. Mechanical as well as optical 3D scanners can be used. In case of optical scanners, laser sheet scanners as well as structured-light scanners can be used. In order to obtain the inner tooth structure, for example, the outer enamel layer consisting of inorganic substances (hydroxyapatite, fluoroapatite, $CaPO_3$) is etched away by means of acids, preferred hydrofluoric acid (HF). Since the inner dentin core and the dental pulp ("dental nerve") located further inside consist mainly of organic substances, e.g. proteoglycans, the inner tooth geometry is maintained as scaffold and thus can be scanned. Due to the presence of areas which are not changed by the etching process, in particular in the region of the root, a digital allocation (the so-called "matching") of outer and inner geometry can take place.

Furthermore, it is possible to record the outer tooth geometry and the layered inner tooth geometry by means of micro CT and to make these data available as 3D data set in the tooth database.

It is also possible, by mechanically removing layers in a controlled manner and two-dimensionally recording the cut surfaces, to create a three-dimensional tooth geometry with inner and outer structure and to store the same in a tooth database.

It is principally also possible to record the three-dimensional structure of natural teeth by photographing from different camera positions or simultaneously photographing by means of a plurality of cameras from different positions (photogrammetry), wherein, in particular for a better recording of the inner tooth geometry, the tooth to be recorded can be illuminated by means of a light source (e.g. UV light, daylight, blue light, special photoflashes etc.) so as to enhance the contrast, in particular also from the side facing away from the camera. This approach has the advantage that no extracted teeth are necessary, but a large number of natural teeth can be recorded in a non-destructive manner and within a very short time.

It is principally possible to record the outer tooth geometry by means of an intraoral scanner, thus a scanner which records a 3D image within the mouth, in particular by using structured-light projection, laser light sheet projection and/or contrast depth measurement. When using a different wavelength for the light projection or laser sheet projection, the light penetrates through the transparent enamel into the tooth and is reflected only on a deeper layer, in particular the dentin layer. Accordingly, the 3D data generated by this approach represent the inner tooth structure, thus in particular the dentin core of the tooth, in three-dimensional manner.

It is principally also conceivable to determine the outer and inner tooth geometry by further physical recording methods, in particular recording by means of sonography (ultrasonic), X-ray radiation, radioactive radiation, etc.

Another possibility is generating three-dimensional data of outer and inner tooth geometry by manual production by the dental technician or by means of RP methods. When carrying out this variant, impressions of natural teeth are taken and two-dimensional photos are taken of the individual teeth on which the dentin and incisal regions are clearly visible. The impressions are filled with superhard plaster and the teeth are individually separated by the dental technician. Subsequently, this outer geometry is three-dimensionally recorded by 3D scanning In a subsequent step, the dental technician reduces the outer geometry by means of the "cut back" method by removing material, in particular by means of milling down to the dentin core, wherein the dental technician uses the two-dimensional photos as reference during the "cut back". Subsequently, the inner tooth structure is recorded three-dimensionally by 3D scanning and, by means of non-machined tooth areas, combined with the outer tooth shape. Furthermore, to make work easier, it is also possible to duplicate the individual plaster teeth and to cast them in wax. This allows an easy reduction of the outer tooth geometry by means of wax knives or cut back instruments. The most advanced possibility is the production of outer wax or plastic geometries by means of 3D data of teeth, which data have been generated by intraoral scanning These data are then converted by means of milling processes or RP processes (Rapid Prototyping) into a real geometry (e.g. in wax or plastic) and can now be further processed by the dental technician using the cut back method and the tooth geometry can be three-dimensionally scanned and combined with the outer geometry.

The knowledge underlying the present invention lies in the ability to record, in addition to the outer tooth structures, also the layered inner tooth geometries and to use them together with the outer tooth geometries and, for example, to store them in a database. It is particularly advantageous if the outer tooth structures and the layered inner tooth structures are dynamically interconnected so that in case of a virtual shape change of the outer geometry, the inner tooth structure can be changed at the same time. A further advantageous aspect is that due to the digital recording of a large number of three-dimensional outer and inner tooth geometries it is possible to provide a fixed relationship between layered inner tooth structure and the outer tooth shape. Furthermore, according to the invention, when selecting a suitable outer geometry, the database can be enabled to provide the user with a proposal for an inner tooth geometry which corresponds with high probability to the natural inner tooth geometry of the natural tooth.

The inventors identified a relationship between outer and inner tooth geometry, for example that certain shape types (e.g. oval, square, triangular) indicate characteristic inner tooth structures (e.g. distinct mamelon structures in case of large triangular teeth). The invention makes it possible to capture said knowledge in thee-dimensional digital form as dynamic database.

The three-dimensional data sets of a plurality of natural teeth digitally recorded for example with the methods described above are advantageously stored in the database with their outer tooth geometry as well as with their layered inner tooth structure. Likewise, in the same manner, data sets which are generated by manual preparatory work and subsequent three-dimensional digital recording can be stored in the data base.

It is also possible to digitally and three-dimensionally record data sets of fully toothed jaw sections such as, for example, the entire fully toothed upper anterior jaw region (from canine to canine), the entire lower anterior jaw (from canine to canine) as well as in each case the 4 posterior tooth segments of upper and lower jaws (from $1^{st}$ premolar to $3^{rd}$ molar). Between the data sets of the individual teeth, a mathematical operation is created so that a master data set is generated which contains the data sets of all individual teeth of the jaw section. Thus, to each tooth type from the jaw section, a correlating other tooth type from the same jaw section can be allocated.

Allocating scanned teeth to the different tooth types (middle incisor, posterior incisor, canine, $1^{st}$ and $2^{nd}$ premolar, $1^{st}$, $2^{nd}$ and $3^{rd}$ molar) is carried out, for example, individually by the programmer. A further subdivision of the respective tooth types into different shape groups can take place by evaluating tooth-specific surface and shape features. Said feature can be, for example:
  mesiodistal curvature
  incisal-cervical curvature
  rounding of the distal incisal edge
  rounding of the mesial incisal edge
  angle feature
  incisal edge line
  surface structure elements such as longitudinal grooves or elevations Grouping the scanned data sets in different shape groups can be carried out by visual evaluation or digitally by means of a "best fit alignment" calculation. In both cases, the result is a tooth database which has a subdivision of the different tooth types into a plurality of shape groups.

In the same manner it is also possible to allocate the digitally recorded inner tooth structures (in particular dentin core structures) of the different tooth types (middle incisor, posterior incisor, canine, $1^{st}$ and $2^{nd}$ premolar, $1^{st}$, $2^{nd}$ and $3^{rd}$ molar) with the aforementioned method to different shape groups. Here too, the allocation is carried out by visual evaluation or, for example, by "best fit alignment" calculation. Here, a database is created which has a classification into different shape groups. In addition, it is possible to establish a correlation between inner tooth geometries and outer tooth geometries. For a particular outer tooth shape, a proposal for an inner tooth geometry is made with the aid of the database, which proposal corresponds with high probability to the real inner tooth geometry. Said probability is higher, the more data sets are contained in the tooth database.

Here, as a novel application, it is also possible to use the biogeneric tooth model. In this case, an average inner geometry (for example dentin core) is calculated from the plurality of available different data sets from the database, which average inner geometry has all the features of the inner tooth geometry which are characteristic for the respective tooth type. There is no pure superposition of each of the individual points $(x_n, y_n, z_n)$ which describe the inner tooth geometry because this would result in a noisy, unstructured data set which does not correspond at all to a typical inner tooth geometry. Instead, the "dentin core" is split into individual components (mamelon structures, incisal grooves, incisal extension of the dentin core, etc.) so as to find "correspondences" in order to average like with like. This prevents that essential structures of the "dentin core" are averaged out when forming the average geometry as this is takes place in case of conventional superposition, for example in case of the mamelon structures. With this method, an "average inner tooth geometry" with the averaged values of the characteristic components such as mamelon structures, incisal grooves, incisal edge, etc. is obtained.

In the next step, the deviation of the individual inner geometries from the average inner geometry is determined by principal component analysis. If eventually an inner layered tooth structure is to be reconstructed, the biogeneric tooth model is linked here with the outer tooth geometry. In this case, the layered inner tooth structure, in particular the dentin core, corresponds to the missing tooth substance in case of the biogeneric inlay reconstruction. A certain spatial distribution of a few construction points on the outer tooth surface results in a certain morphology of the dentin core. The combination of the "average dentin core" with the biogeneric model of the outer tooth makes it possible with high probability to allocate the most suitable dentin core to a predefined outer tooth geometry. In its fundamental configuration, the morphological relationship between outer tooth geometry and the layered inner tooth structure is based on a genetically determined blueprint so that with a high probability, a layered inner tooth structure can be allocated to a certain outer tooth geometry, and a certain outer tooth geometry can be allocated in particular to the dentin core and vice versa.

After digitally linking the outer tooth geometry with the inner tooth geometry, a correlation is being created between these two data sets which can be dynamic and/or static. In case of a static linkage, the inner geometry is not changed after a change of the outer geometry, i.e., that, e.g., the dentin core remains in the same shape. In contrast, in case of a dynamic correlation, the inner tooth structure is changed proportionally together with the outer tooth surface. All X, Y, Z values of the inner tooth geometry change when enlarging or reducing the size of the outer tooth geometry with the same factor as the X, Y, Z values of the outer tooth geometry (scaling). A rotation takes place with the same angular dimension and a translation takes place with the same X, Y, Z values by adding up the translation values.

The use of this database with correlation between inner and outer tooth geometry (correlation database) offers different possibilities for producing tooth replacement parts. By means of computer-assisted output devices (CNC, RP), tooth replacement parts are produced which simulate the layered inner structure of the natural tooth. The inner structure of the tooth replacement part is produced on the basis of a data set from the database, wherein the part's outer surface corresponds exactly to the inner tooth structure of a data set selected from the database. As materials for producing the inner structure, materials are used which have a tooth-like aesthetic with respect to color and translucence, in particular plastics, glass-ceramics, feldspar ceramics, lithium silicate ceramics as well as oxidic high-performance ceramics such as, for example, zirconium dioxide and aluminum oxide. Onto said computer-produced inner structure of the tooth replacement part, subsequently, the so-called incisal region is built up. This can be carried out manually, e.g. by coating or growing and overpressing. It is also possible that said incisal region is generated by calculating the difference of the data sets of outer tooth surface and inner tooth structure and thus is available as data set and a real geometry can be produced by computer-assisted methods. In a subsequent joining step, this incisal region is applied onto the dentin core, in particular by sintering by means of a ceramic connector compound, by polymerizing or adhesive bonding.

If dental restorations are to be prepared for a patient, according to the invention, there is a plurality of possibilities to digitally design and produce said restorations. Examples are described below.

The jaw situation with the teeth to be replaced as well as the adjacent teeth is recorded by 3D scanning (intraoral or extraoral) and digitalized. If mirror-imaged teeth are present, the three-dimensional structures of the same are mirrored. It was found that the mirror-symmetrical replacement of anterior teeth is satisfying with respect to proximal, occlusal and aesthetic aspects. The outer structure of the mirrored tooth is now compared and integrated by iterative processes with a plurality of stored data of natural teeth and manually prepared teeth until the most suitable data set is found. For determining the suitable data set by iterative processes, a similarity measure can be formed which results from the standard deviation of the values of the shortest distance from points of the surface of the mirrored tooth with respect to each of the respective nearest points of the respective tooth data sets from the database.

A standard deviation stddev of the shortest distance as similarity measure can be calculated for example as:

$$stddev = \sqrt{\frac{\sum_{i,j}^{n}[(x_{1i}-x_{2j})+(y_{1i}-y_{2j})+(z_{1i}-z_{2j})]^2}{n}}$$

This approach is also called "best fit superposition" ("best fit alignment"). In order to achieve the "best fit alignment", the tooth is mirrored and subsequently superimposed by rotation, translation and potentially also size scaling in the most optimal position with the tooth to be compared from the database. For this, image analysis programs can be used (e.g. Geomagic GmbH Köln, Germany). Since for the most suitable data set, an inner layered tooth structure exists, the same can be used for producing the tooth replacement, in particular for producing a dentin core by means of computer-assisted methods. Once the dentin core is prepared, the incisal region can be manually applied onto the same, or an incisal region prepared by means of computer-assisted production can be connected to the dentin core by adhesive bonding, sintering or polymerizing.

The jaw situation with the teeth to be replaced and the adjacent teeth is recorded by 3D scanning (intraoral or extraoral) and digitalized. If no mirror image teeth are present in this jaw, a data set is selected which is suitable according to the user's discretion and can be adapted by the user in a three-dimensional manner by rotation (turning), translation (displacing) and scaling (size change). Due to the dynamic correlation of the data set of the three-dimensional outer tooth geometry with the data set of the three-dimensional inner layered structure, an inner layered structure, e.g. a dentin core is proposed to the user. An individual modification of said proposed dentin core by the user is also possible. Subsequently, the three-dimensional data of the layered inner structure, in particular the dentin core, is converted on a computer-assisted output device, in particular CNC milling machine, RP machine, into a real geometry. Once the dentin core is prepared, the incisal region can be manually applied onto the same or an incisal region prepared by means of computer-assisted production can be connected to the dentin core by adhesive bonding, sintering or polymerizing.

The jaw situation with the teeth to be replaced and the adjacent teeth is recorded by 3D scanning (intraoral or extraoral) and digitalized. If no mirror image teeth are present in this jaw, the remainder of the teeth is compared by the computer-assisted program with the data sets from the database of the jaw sections and therefrom, the most suitable data set is selected by means of "best fit alignment". Since exactly to this data set a data set of the missing tooth is allocated, said data set can serve as the basis for the tooth to be replaced. Due to the dynamic correlation of the three-dimensional outer tooth geometry with the three-dimensional inner layered structure, an inner layered structure, e.g. a dentin core is proposed to the user. An individual modification of said proposed dentin core by the user is also possible. Subsequently, the three-dimensional data set of the layered inner structure, in particular the dentin core, is converted on a computer-assisted output device, in particular CNC milling machine, RP machine, into a real geometry. Once the dentin core is prepared, the incisal region can be manually applied onto the same or an incisal region prepared by means of computer-assisted production can be connected to the dentin core by adhesive bonding, sintering or polymerizing.

A further use of the present invention is that the described database, the described tooth model and the described method are used for identifying live and dead beings. For this, data sets of the natural and/or artificial teeth of the beings to be identified can be compared with the data sets of the natural and/or artificial teeth from the database and checked for maximum correspondence. For example, due to the mastication or brushing the teeth, a certain wear occurs on the outer tooth surfaces. Therefore, for identification, in particular those regions of the outer tooth surfaces are suitable which are not or only minimally subjected to said wear. These are in particular such surfaces of natural teeth which face toward the palate and the tongue (palatal and lingual surfaces). Since the inner layered tooth structures are not subjected to any mechanical wear, the same are also suitable for identification. However, the regions of the dental pulp are not suitable because the same become smaller with increasing age. In contrast, the structures of the dentin core can be considered suitable. Due to the uniqueness (each outer tooth surface and each dentin core exists only once in the world), the use of the data sets of the described structures of natural teeth for the purpose of identification can also be dedicated as "dental fingerprint".

The invention claimed is:

1. A method for producing a tooth replacement comprising the generation of the tooth replacement having in particular a one-piece core and in particular a one-piece outer layer, wherein the core and the outer layer define a boundary surface between each other,
    wherein
    an extension of the boundary surface represents a dentino-enamel junction of a tooth for which the tooth replacement is provided,
    wherein the extension of the boundary surface
    (i) is determined based on a recording of the dentino-enamel junction of the tooth for which the tooth replacement is provided, and/or
    (ii) is determined based on directly or indirectly recorded geometry data of at least a portion of the outer geometry of the tooth for which the tooth replacement is provided,
    wherein the material or the materials for core and outer layer are selected such and/or generating core and outer layer is carried out such that a translucence of the outer layer is higher than the translucence of the core.

2. The method according to claim 1, wherein recording the dentino-enamel junction of the tooth takes place by means of computer tomography, in particular microcomputer tomography, sonography, radiography, close-range photogrammetry and/or photography.

3. The method according to claim 1, wherein the indirectly recorded geometry data are determined from geometry data of the situation of the remainder of the teeth.

4. The method according to claim 1, wherein determining the extension of the boundary surface comprises:
    virtually deforming the outer model geometry of a predetermined tooth data set for adapting to the outer geometry of the tooth for which the tooth replacement is provided, and
    virtually deforming a model boundary surface of the predetermined tooth data set corresponding to the deformation of the outer geometry for determining the boundary surface.

5. The method according to claim 1, wherein determining the extension of the boundary surface comprises:
    determining a group of tooth data sets, wherein a predetermined average value of the outer model geometry of the group of tooth data sets corresponds to the outer geometry of the tooth for which the tooth replacement is provided, and
    determining the extension of the boundary surface by means of the predetermined average value of model boundary surfaces of the group of tooth data sets.

6. The method according to claim 5, wherein the average value is determined by averaging the absolute and/or relative positions of predetermined reference points.

7. The method according to claim 1, wherein determining the extension of the boundary surface comprises:
    determining a tooth data set, the outer model geometry of which meets a predetermined similarity criterion with respect to the outer geometry of the tooth for which the tooth replacement is provided, and
    determining the extension of the boundary surface based on the model boundary surface of the tooth data set.

8. The method according to claim 1, wherein the model boundary surface of at least one tooth data set is determined based on a recording of the dentino-enamel junction of a natural tooth by means of computer tomography, in particular microcomputer tomography, sonography, radiography, close-range photogrammetry and/or photography and/or a recording of the outer geometry of the dentin of a natural tooth after removing the enamel.

9. The method according to claim 2, wherein recording the dentino-enamel junction takes place by means of close-range photogrammetry and/or photography using light for which the enamel of the tooth is translucent, in particular using red light or light having a longer wavelength.

10. The method according to claim 1, wherein the translucence of the core lies in the range from 20 to 65%, and the translucence of the outer layer lies in the range from 65 to 95%.

11. The method according to claim 1, wherein the core comprises or consists of an oxide-ceramic material, a silicate-ceramic material and/or a plastic material, and/or
    the outer layer comprises or consists of an oxide-ceramic material, a silicate-ceramic material and/or a plastic material.

12. A non-transitory storage device comprising machine-readable instructions for carrying out a method according to claim 1.

13. A non-transitory computer readable storage media containing executable instructions which cause a device according to claim 12 to carry out a method according to claim 1 when the instructions are carried out on the device.

14. The method according to claim 1, wherein the translucence of the core lies in the range from 40 to 60% and the translucence of the outer layer lies in the range from 67.5 to 85%.

* * * * *